United States Patent
Heffels et al.

(10) Patent No.: US 11,237,141 B2
(45) Date of Patent: Feb. 1, 2022

(54) GAS ANALYZER FOR MEASURING NITROGEN OXIDES AND SULFUR DIOXIDE IN EXHAUST GASES

(71) Applicant: SIEMENS AKTIENGESELLSCHAFT, Munich (DE)

(72) Inventors: Camiel Heffels, Stutensee-Buechig (DE); Jochen Lang, Karlsruhe (DE); Benjamin Schmidt, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 173 days.

(21) Appl. No.: 16/635,713

(22) PCT Filed: Jul. 18, 2018

(86) PCT No.: PCT/EP2018/069486
§ 371 (c)(1),
(2) Date: Jan. 31, 2020

(87) PCT Pub. No.: WO2019/025186
PCT Pub. Date: Feb. 7, 2019

(65) Prior Publication Data

US 2021/0132019 A1    May 6, 2021

(30) Foreign Application Priority Data

Jul. 31, 2017   (DE) .......................... 102017213196

(51) Int. Cl.
*G01N 33/00*    (2006.01)
*F01N 11/00*    (2006.01)

(52) U.S. Cl.
CPC ..... *G01N 33/0037* (2013.01); *G01N 33/0042* (2013.01); *F01N 11/007* (2013.01);
(Continued)

(58) Field of Classification Search
CPC ........... G01N 33/0037; G01N 33/0042; G01N 21/33; G01N 21/3504; G01N 2201/062;
(Continued)

(56) References Cited

U.S. PATENT DOCUMENTS 5,806,305 A    9/1998  Miller et al.
9,863,267 B2 *  1/2018  O'Dea ...................... F23R 3/28
(Continued)

FOREIGN PATENT DOCUMENTS

CN    105424631    3/2016
DE    202017001743    5/2017
(Continued)

OTHER PUBLICATIONS

Higashi Ryoichi et al.: "A NOx and SO2 gas analyzer using deep-UV and violet light-emitting diodes for continuous emissions monitoring systems", Proc. SPIE 9003, Light-Emitting Diodes: Materials, Devices, and Applications for Solid State Lighting XVIII, 90031F, pp. 1-6; 2014.
PCT International Search Report dated Oct. 4, 2018 based on PCT/EP2018/069486 filed Jul. 18, 2018.

*Primary Examiner* — Freddie Kirkland, III
(74) *Attorney, Agent, or Firm* — Cozen O'Connor (57) ABSTRACT

A gas analyzer via which exhaust gas to be analyzed is conducted untreated through a first measurement chamber and, after treatment in an oxidation device, through a second measurement chamber, wherein ozone is produced from oxygen to thereby convert nitrogen monoxide into nitrogen dioxide, where the gas analyzer has a first light emitting diode and a second light emitting diode, light of both diodes is conducted through the first measurement chamber onto a first detector, light of the first light emitting diode is partly conducted through the second measurement chamber onto a second detector via a beam splitter arrangement, based on the first detector signal, the nitrogen dioxide concentration
(Continued)

of the untreated gas is also measured, based on the second detector signal, the nitrogen dioxide concentration of the treated exhaust gas is measured, and the nitrogen oxide concentration of the exhaust gas is additionally determined from measured nitrogen dioxide concentrations.

9 Claims, 5 Drawing Sheets

(52) U.S. Cl.
CPC .. *F01N 2560/026* (2013.01); *F01N 2560/027* (2013.01); *F01N 2900/1402* (2013.01)

(58) Field of Classification Search
CPC ............. F01N 11/007; F01N 2560/026; F01N 2560/027; F01N 2900/1402; F01N 11/00; Y02A 50/20; Y02T 10/40
See application file for complete search history.

(56) References Cited

U.S. PATENT DOCUMENTS

| | | | |
|---|---|---|---|
| 10,871,443 B2 * | 12/2020 | Heffels | ................. G01N 21/85 |
| 11,060,969 B2 * | 7/2021 | Heffels | .............. G01N 33/0037 |
| 2011/0177607 A1 | 7/2011 | Akasaka et al. | |
| 2013/0045541 A1 | 2/2013 | Fix et al. | |
| 2016/0010493 A1 | 1/2016 | O'Dea et al. | |
| 2019/0317067 A1 * | 10/2019 | Heffels | ................. G01N 31/005 |
| 2021/0109014 A1 * | 4/2021 | Heffels | .............. G01N 33/0042 |

FOREIGN PATENT DOCUMENTS

| | | |
|---|---|---|
| EP | 1020620 | 7/2000 |
| EP | 2157421 | 2/2010 |
| JP | 60119443 | 6/1985 |
| JP | 2012026331 | 2/2012 |
| WO | 2015181879 | 4/2017 |

* cited by examiner

GAS ANALYZER FOR MEASURING NITROGEN OXIDES AND SULFUR DIOXIDE IN EXHAUST GASES

CROSS-REFERENCE TO RELATED APPLICATIONS

This is a U.S. national stage of application No. PCT/EP2018/069486 filed Jul. 18, 2018. Priority is claimed on German Application No. 102017213196.9 filed Jul. 31, 2017, the content of which is hereby incorporated by reference in its entirety.

BACKGROUND OF THE INVENTION

1. Field of the Invention

The invention relates to a gas analyzer for measuring nitrogen oxides and sulfur dioxide in an exhaust gas, having a first light-emitting diode radiating in the near-ultraviolet range (NUV) between 350 nm and 500 nm, a second light-emitting diode radiating in the middle-ultraviolet range (MUV) between 250 nm and 300 nm, a first measuring chamber, through which the exhaust gas flows and which is irradiated by the light of both light-emitting diodes, a first detector, which detects the light of both light-emitting diodes after irradiation of the measuring chamber and which generates a first detector signal with a first signal component resulting from the light of the first light-emitting diode and a second signal component resulting from the light of the second light-emitting diode, an evaluation device that uses the first signal component to ascertain the concentration of nitrogen dioxide and uses the second signal component to ascertain the concentration of sulfur dioxide in the exhaust gas in the first measuring chamber, and an oxidation device that treats the exhaust gas with ozone to convert nitrogen monoxide contained in the exhaust gas into nitrogen dioxide.

2. Description of the Related Art

A gas analyzer for measuring nitrogen oxides and sulfur dioxide in an exhaust gas is known from Ryoichi Higashi et al.: "A NOx and SO2 gas analyzer using deep-UV and violet light-emitting diodes for continuous emissions monitoring systems", Proc. SPIE 9003, Light-Emitting Diodes: Materials, Devices, and Applications for Solid State Lighting XVIII, 90031F (Feb. 27, 2014). Prior to analysis, the exhaust gas is treated in two stages, where in a first stage, with the aid of ozone, nitrogen monoxide contained in the exhaust gas is converted into nitrogen dioxide, which can be measured using the gas analyzer. The ozone is generated from atmospheric oxygen via electrical discharging and is supplied to the exhaust gas. In a second treatment stage, the exhaust gas is heated to around 300° C., in order to thermally decompose excess ozone and dinitrogen pentoxide (N2O5), which results from the reaction of nitrogen dioxide and ozone and cannot be measured by the gas analyzer, into nitrogen dioxide. The concentration of nitrogen dioxide ascertained by the gas analyzer is thus a measure of the concentration of nitrogen oxides in the exhaust gas.

In the conventional gas analyzer, a MUV light-emitting diode with an emission wavelength of 280 nm and a NUV light-emitting diode with an emission wavelength of 400 nm are arranged close to one another in an LED array. A collimator lens is used to shape their light into a parallel light bundle, which irradiates a measuring chamber through which the treated exhaust gas flows and subsequently is focused on a detector. With a beam splitter between the collimator lens and measuring chamber, part of the light is diverted to a monitor detector. The light-emitting diodes are switched on and off in turns, in order to detect the sulfur dioxide contained in the exhaust gas at the absorption wavelength 280 nm and nitrogen dioxide at the absorption wavelength 400 nm. The detector signal is normalized with the signal of the monitor detector, before it is evaluated to ascertain the concentration of sulfur dioxide and nitrogen dioxide or nitrogen oxide in the exhaust gas. The temperature of the light-emitting diodes is regulated to a constant value by means of a Peltier element.

U.S. Pat. No. 5,806,305 A discloses a device for catalytic treatment of exhaust gas in internal combustion engines (gasoline or diesel engines), in which ozone is supplied to the exhaust gas before treatment in the catalytic converter. The ozone is generated in an ozone generator from fresh air via UV light, such as a mercury vapor lamp, at a wavelength of 185 nm.

It is known from EP 1 020 620 B1 to generate the ozone for the same purpose from fresh air or the exhaust gas via UV light, microwaves or radio discharge.

It is known from EP 2 157 421 A1, for the purpose of examining the sulfur content of fuels, to burn a sample of the fuel and to determine the concentration of sulfur dioxide in the exhaust gas by way of an ultraviolet fluorescence measuring procedure. In order to avoid the measurement from being impaired by nitrogen monoxide, the exhaust gas is exposed to the light (185 nm) of a low-pressure mercury discharge lamp in a container beforehand, in order to generate ozone from the residual oxygen content and thus to convert nitrogen monoxide into nitrogen dioxide.

SUMMARY OF THE INVENTION

It is an object of the invention to provide a gas analyzer that enables a reliable continuous measurement of nitrogen oxides and sulfur dioxide in exhaust gases with little outlay in terms of devices.

This and other objects and advantages are achieved in accordance with the invention by a gas analyzer in which a second measuring chamber is connected to the oxidation device, through which the treated exhaust gas flows, while the untreated exhaust gas flows through the first measuring chamber, a beam splitter arrangement splits off part of the light of the first light-emitting diode through the second measuring chamber to a second detector, which generates a second detector signal with a first signal component resulting from the light of the first light-emitting diode, and in which the evaluation device further determines the concentration of nitrogen dioxide in the exhaust gas in the second measuring chamber from the first signal component of the second detector signal and outputs this as the concentration of nitrogen oxide in the exhaust gas and outputs the difference in the concentration of nitrogen dioxide ascertained in the two measuring chambers as the concentration of nitrogen monoxide.

For as complete a conversion of nitrogen monoxide into nitrogen dioxide as possible in the oxidation device, the ozone must be generated with a certain degree of excess. In the subsequent thermal decomposition of dinitrogen pentoxide known from the cited publication by Ryoichi Higashi et al., in addition to nitrogen dioxide, it is also possible for undesired nitrogen monoxide to arise again, for which reason the heating of the exhaust gas should occur in a controlled manner. In this context, or due to interference, the thermal decomposition of the excess ozone may also occur on an incomplete basis. In the middle-ultraviolet range used to measure the concentration of sulfur dioxide in the exhaust gas, however, there is a strong overlap in the absorption bands of sulfur dioxide and ozone. However, as the untreated gas flows through the first measuring chamber in accordance with the invention, it is excluded that amounts of ozone interfere with the measurement of the concentration of sulfur dioxide occurring there.

The concentration of nitrogen dioxide in the untreated exhaust gas is measured in the first measuring chamber and, in addition to the original concentration of nitrogen dioxide, the concentration of nitrogen monoxide converted into nitrogen dioxide, is measured in the second measuring chamber. The gas analyzer in accordance with the invention advantageously uses the two to ascertain both the concentration of nitrogen oxide (as a sum of the concentration of nitrogen dioxide and nitrogen monoxide) and the concentration of nitrogen monoxide and thus naturally also the concentration of nitrogen dioxide in the exhaust gas.

In accordance with an advantageous embodiment of the gas analyzer in accordance with the invention, a monitoring and, where required, controlling of the conversion of the nitrogen monoxide contained in the exhaust gas into nitrogen dioxide, which can be measured using the gas analyzer, said conversion being as complete as possible, occurs via a narrowband light source that radiates in the wavelength range of 760 nm to 765 nm being provided, the light thereof being conducted by the beam splitter arrangement through both measuring chambers to the two detectors and resulting in further signal components of the detector signals, and by the evaluation device using the further signal component of the first detector signal to ascertain the concentration of oxygen in the exhaust gas in the first measuring chamber and using the further signal component of the second detector signal to ascertain the concentration of oxygen in the exhaust gas in the second measuring chamber and, on the basis of both ascertain concentrations of oxygen, monitoring the conversion of the nitrogen monoxide into nitrogen dioxide. The concentration of oxygen in the untreated exhaust gas is measured in the first measuring chamber and the concentration of oxygen in the exhaust gas after the generation of the oxygen and conversion of nitrogen monoxide into nitrogen dioxide taking place accordingly is measured in the second measuring chamber. The difference between both measurements represents the amount of oxygen consumed as part of the conversion NO+O3->NO2+O2 and is therefore a measure of the degree of conversion. If the ozone is not exclusively generated from the residual oxygen content of the exhaust gas, then for example the additional oxygen supplied (e.g., atmospheric oxygen) can initially be guided through the first measuring chamber with the exhaust gas, where it is measured, before it reaches the oxidation device.

The narrowband light source may, e.g., involve a wavelength-tunable laser diode or a light-emitting diode with a downstream filter, e.g., interference filter. The wavelengths of the light generated by the laser diode may be tuned in a known manner via an absorption line of the oxygen, where the light detected by the detectors (here the further signal components of the detector signals) are evaluated on a wavelength-dependent basis, e.g., in accordance with the method of direct absorption spectroscopy or wavelength modulation spectroscopy.

For referencing (normalizing) the measurements, the beam splitter arrangement is preferably formed to split off part of the light of the two light-emitting diodes and, if present, the narrowband light source to a reference detector, which generates a reference signal using the reference signal components resulting from the light of the light-emitting diodes and, where required, the narrowband light source. The referencing of the signal components of the detector signals with the associated reference signal components then occurs in the evaluation device, for example, by forming a quotient. In order to be able to differentiate the different signal components of the detector signals and reference signal components in the case of light-emitting diodes, the light-emitting diodes can be actuated with time-division multiplexing one after the other or their light can be modulated differently on generation and demodulated on detection, e.g., in a phase-sensitive manner.

The ozone generation in the oxidation device may occur in various ways: The ozone generation from atmospheric oxygen via electrical discharging (corona discharge) mentioned in the publication by Ryoichi Higashi et al. has the disadvantage that nitrogen oxide compounds form that are undesirable for measuring the nitrogen oxide in the exhaust gas. The oxidation device of the gas analyzer in accordance with the invention therefore preferably has an ozone generator with an ultraviolet light source generating high-energy radiation with a wavelength smaller than 240 nm, for example, an electrode-free excimer lamp or a low-pressure mercury discharge lamp, a reaction chamber through which the exhaust gas flows and a heating chamber downstream of said reaction chamber. With lean combustion with an excess of air, the ozone can be completely generated from the residual oxygen content of the exhaust gas. Here, the ozone generator is arranged in the reaction chamber through which the exhaust gas flows and which is closed to the outside. The reaction chamber may, e.g., be established in the form of an inwardly mirrored tube (e.g., aluminum tube), in which the ultraviolet light source, which may be cylindrical, for example, extends. In order to increase the performance when converting nitrogen monoxide into nitrogen dioxide, a plurality of such tubes may be connected in parallel. If the performance of the ultraviolet light source declines over time, then the exhaust gas can be additionally supplied with atmospheric oxygen. As already explained, the oxygen contained in the untreated exhaust gas (residual oxygen and, where required, supplied oxygen) can be measured in the first measuring chamber.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

To further explain the invention, reference is made below to the figures in the drawing, in which.

DETAILED DESCRIPTION OF THE EXEMPLARY EMBODIMENTS

Identical parts and parts having an identical effect are provided with the same reference characters in each case.

Figure 1:
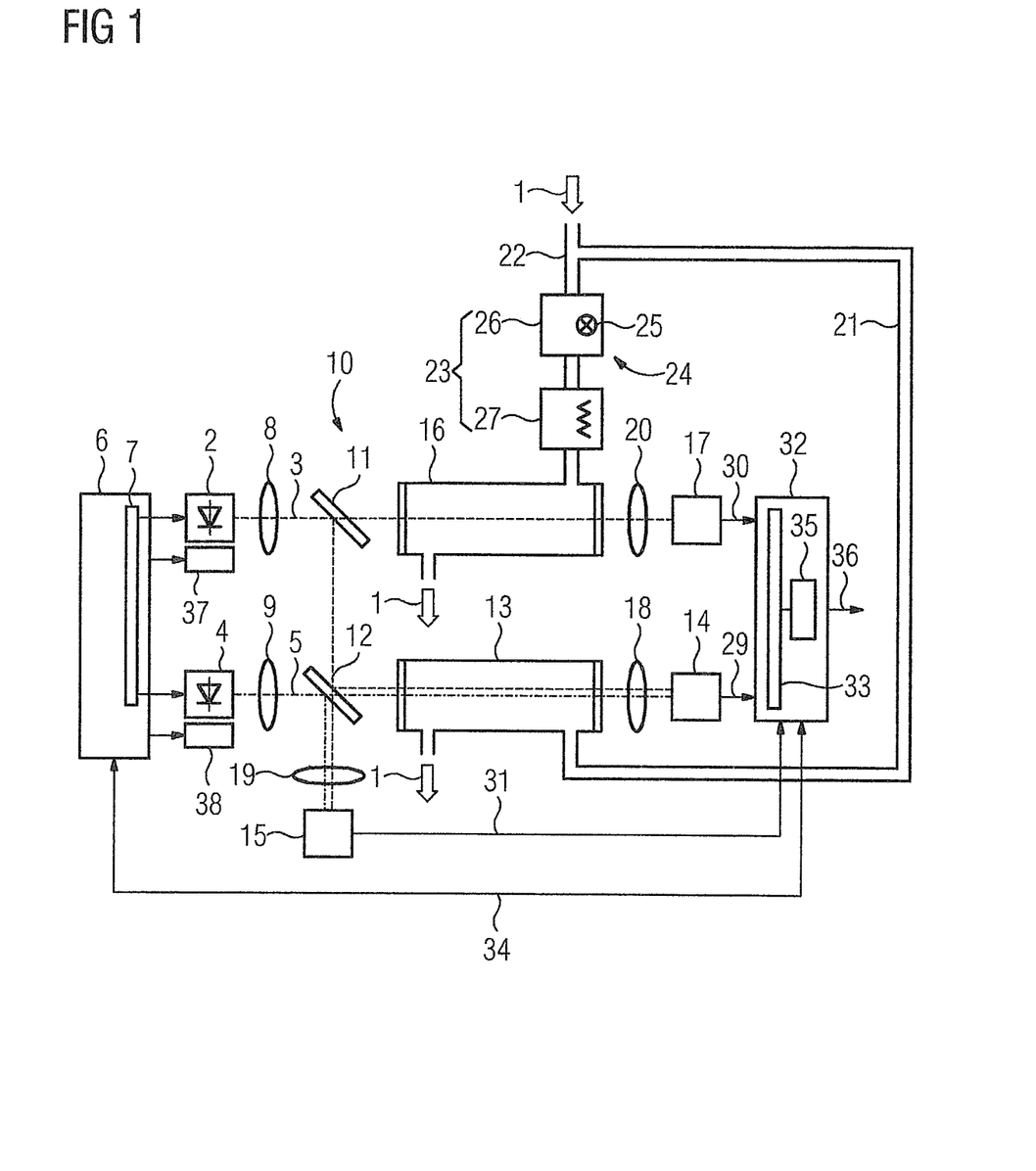
FIG. 1 shows a first exemplary embodiment of the gas analyzer in accordance with the invention for measuring nitrogen oxides and sulfur dioxide.

FIG. 1 shows a simplified schematic representation of a block circuit diagram of a gas analyzer for measuring nitrogen oxides and sulfur dioxide in an exhaust gas 1. A first light-emitting diode 2 generates light 3 in the near-ultraviolet range between 350 nm and 500 nm, such as around 405 nm. A second light-emitting diode 4 generates light 5 in the middle-ultraviolet range between 250 nm and 300 nm, such as 285 nm +/−20 nm. Both light-emitting diodes 2, 4 are actuated by a control device 6, which in the exemplary illustrated embodiment contains a multiplexer 7, in order to switch the light-emitting diodes 2, 4 on and off in an alternating manner. The light 3, 5 emitted by the light-emitting diodes 2, 4 is shaped with the aid of collimator lenses 8, 9 to form parallel light bundles (referred to as light beams below) and supplied to a beam splitter arrangement 10 with two semi-transparent mirrors 11, 12, preferably "polka-dot" beam splitters with a constant reflection/transmission ratio over a large spectral range. The first mirror 11 reflects part of the light beam 3 of the first light-emitting diode 2 to the second mirror 12, which splits this part of the light 3, together with the light 5 of the second light-emitting diode 4, into a partial beam through a first measuring chamber 13 to a first detector 14 and a further partial beam to a reference detector 15. The part of the light 3 allowed to pass through the first partial mirror 11 irradiates a second measuring chamber 16 and subsequently strikes a second detector 17. The respective partial beams are focused on the detectors 14, 15, 17, which involve photodiodes in this case, with the aid of lenses 18, 19, 20.

After a pretreatment (not shown here), which comprises dehumidification via gas cooling and the separation of condensate, as well as a fine filtering of particles, the exhaust gas 1 is split into two partial flows, of which the one partial flow is conducted directly into the first measuring chamber 13 via a first gas line 21, while the other partial flow is initially conducted via a second gas line 22 through an oxidation device 23, before it reaches the second measuring chamber 16. Once they have passed through the respective measuring chamber 13 or 16, both partial flows of exhaust gas are conducted out therefrom. The overall flow or the two partial flows are able to be set and kept constant in a known manner by regulating the pressure or flow rate.

The oxidation device 23 has an ozone generator 24 in the form of an ultraviolet light source 25 in a closed reaction chamber 26 through which the exhaust gas 1 flows, and a subsequent heating chamber 27. The ultraviolet light source 25 uses its radiation of 185 nm, for example, to generate ozone from the residual oxygen of the exhaust gas 1, where the ozone converts nitrogen monoxide contained in the exhaust gas 1 into nitrogen dioxide in the reaction chamber 26. Nitrogen dioxide also reacts with the generated ozone, however, resulting in further nitrogen oxides, primarily dinitrogen pentoxide. In the heating chamber (gas heater) 27, these undesirable nitrogen oxides and excess ozone are thermally decomposed at around 300° C. to form nitrogen dioxide and oxygen.

Figure 2:
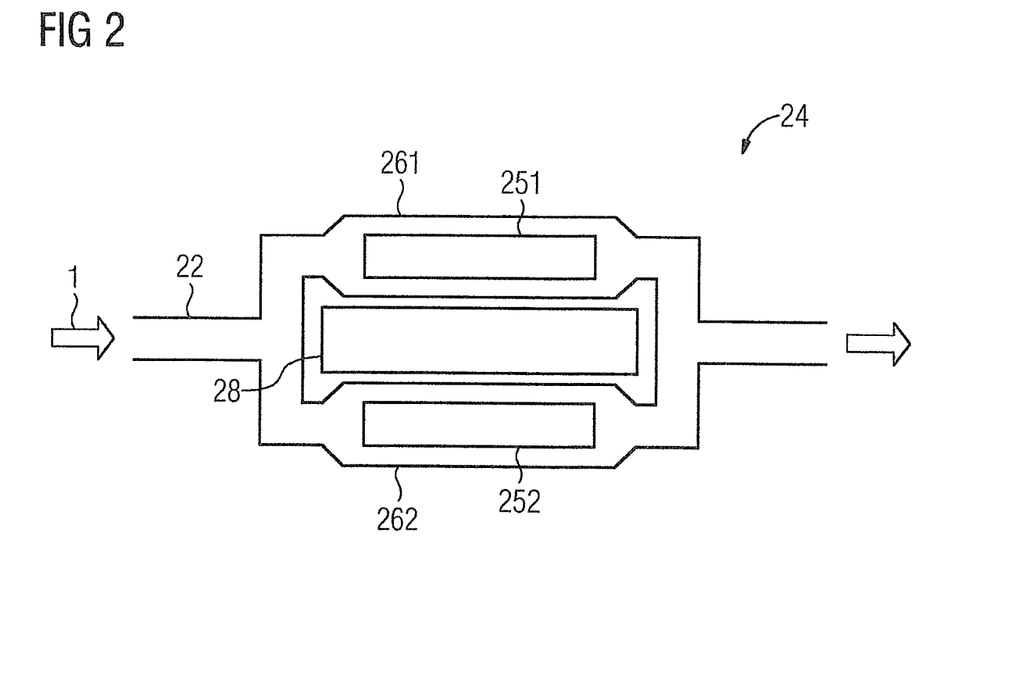
FIG. 2 shows an exemplary embodiment of an ozone generator in accordance with the invention.

FIG. 2 shows a highly simplified exemplary embodiment of the ozone generator 24 with two ultraviolet light sources 251, 252, here in the form of cylindrical low-pressure mercury discharge lamps, which are arranged in two inwardly mirrored aluminum tubes 261, 261 connected in parallel, through which the exhaust gas 1 flows. The tubes 261, 262 form the reaction chamber 26. The excitation of the mercury plasma can occur via electrodes or, in order to increase the service life, without electrodes via a microwave generator 28.

Figure 3:
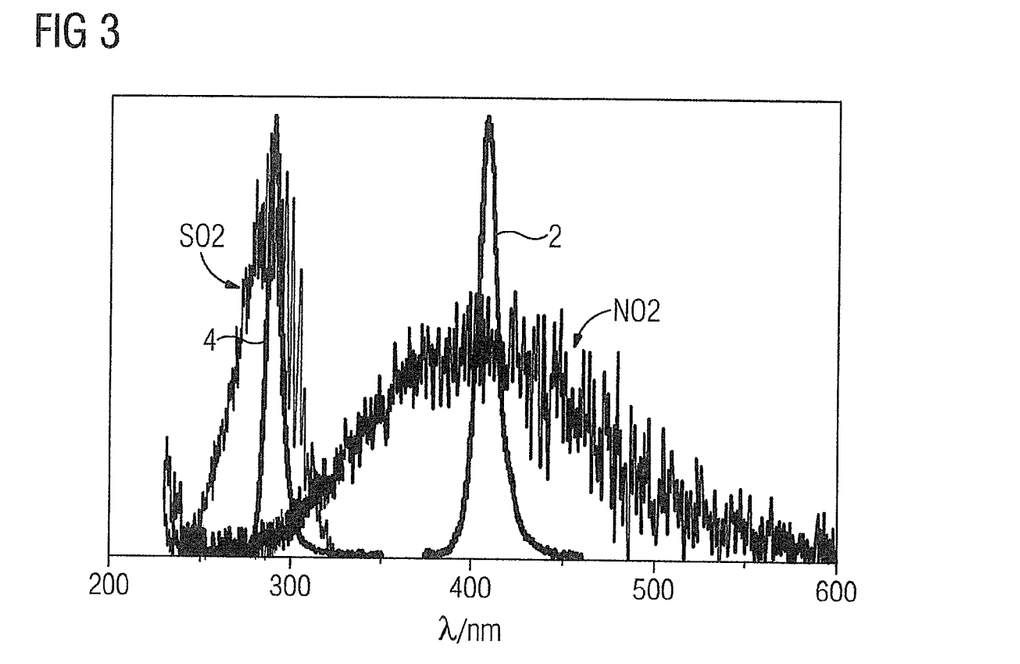
FIG. 3 shows an exemplary graphical plot of the absorption spectra of nitrogen dioxide and sulfur dioxide, as well as the absorption spectra of the light-emitting diodes of the gas analyzer.

FIG. 3 shows, by way of example, a graphical plot of the absorption spectra of nitrogen dioxide NO2 and sulfur dioxide SO2, the emission spectrum of the first light-emitting diode 2 at 405 nm and the emission spectrum of the second light-emitting diode 4 at 285 nm.

Returning to FIG. 1, the first detector 14, which detects the light 3, 5 of the light-emitting diodes 2, 4 once the untreated exhaust gas 1 has flown through the first measuring chamber 13, generates a first detector signal 29, and the second detector 14, which detects the light 3 of the light-emitting diode 2 once the treated exhaust gas 1 has flown through the second measuring chamber 16, generates a second detector signal 30. According to the alternating actuation of the light-emitting diodes 2, 4, the first detector signal 29 consists of two signal components in alternating succession, of which a first signal component results from the light 3 of the first light-emitting diode 2 and a second signal component results from the light of the second light-emitting diode 4. The second detector signal 30 only has a signal component resulting from the light 3 of the first light-emitting diode 2. The reference detector 15 generates a reference signal 31 with reference signal components in alternating succession that result from the light 3, 5 of both light-emitting diodes 2, 4. The detector signals 29, 30 and the reference signal 31 are supplied to an evaluation device 32, which contains a demultiplexer 33 for separating the different signal components. The synchronization of the multiplexer 7 and demultiplexer 33 occurs via a communication line 34 between the control device 6 and the evaluation device 32. Once the signals 29, 30, 31 have been prepared, e.g., filtered and digitized, the first signal component of the first detector signal 29 is used to ascertain the concentration of nitrogen dioxide in the untreated exhaust gas in the first measuring chamber 13 and the second signal component is used to ascertain the concentration of sulfur dioxide in a computing device 35, and these are output as a result 36 of the gas analyses. The second detector signal 30 is used to ascertain the concentration of nitrogen dioxide in the treated exhaust gas in the second measuring chamber 16 and this is output in the result 36 as the concentration of nitrogen oxide in the exhaust gas 1. In this context, the signal components of the detector signals 29, 30 are referenced with the associated signal components of the reference signal 31, so that the analysis result 36 is independent of the brightness of the light-emitting diodes 2, 3 and therefore, e.g., of their aging status. The difference in the concentrations of nitrogen dioxide ascertained in the two measuring chambers 13, 16 corresponds to the concentration of nitrogen monoxide in the exhaust gas 1 and is likewise output.

Despite the mentioned referencing of the measurements, it is advantageous to thermostatically control the entire photometric measuring arrangement of the gas analyzer. This also includes thermostatically controlling the light-emitting diodes 2, 3 with the aid of Peltier elements 37, 38 in order to be able to realize measuring ranges in the lower ppm range.

The gas analyzer shown is readily able to be expanded for the measurement of further constituent parts of the exhaust gas 1, such as carbon dioxide, carbon monoxide, compounds of sulfur, chlorine and iodine. Instead of the further suitable light sources required for this purpose (e.g., light-emitting diodes), it is possible for individual light-emitting diodes already available to be provided with a luminescent material (phosphor), which partially converts the light generated by the light-emitting diode in question into a light with a longer wavelength. This principle is known from US 2010/049017 A1, for example.

Figure 4:
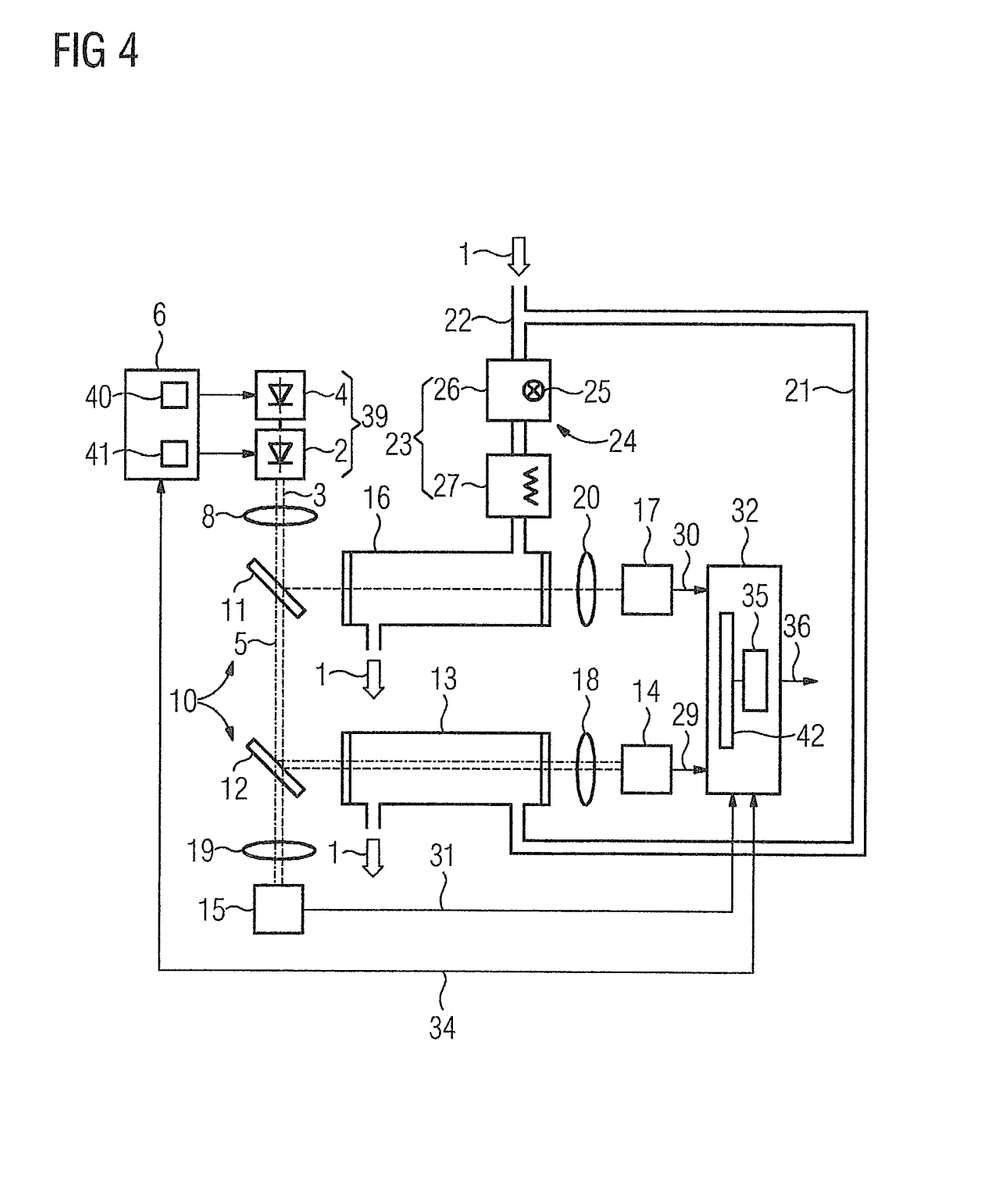
FIG. 4 shows a second exemplary embodiment of the gas analyzer in accordance with the invention for measuring nitrogen oxides and sulfur dioxide.

FIG. 4 shows a second exemplary embodiment of the gas analyzer in accordance with the invention, which differs from that of FIG. 1 by the two light-emitting diodes 2, 4 (and, where required, further light-emitting diodes not shown here) being arranged adjacent to one another in an array 39. The light-emitting diodes 2, 4 are shown in succession here, solely for reasons of improved ease of representation. Instead of two collimator lenses for the different light-emitting diodes 2, 4, only one common collimator lens 8 is required here.

A further difference consists in that the light-emitting diodes 2, 4 are not actuated in multiplex operation, but rather are modulated differently via signal generators 40, 41, e.g., with different modulation frequencies, clock rates or pulse codes. Instead of a demultiplexer, the evaluation device 32 accordingly contains a demodulator 42, which demodulates or decodes the signal components of the detector signals 29, 30 and the reference signal 31 at the different modulation frequencies or clock rates in a phase-sensitive manner, in order to separate the signal components for further processing and evaluation.

The different arrangement of the light-emitting diodes 2, 4 and their different actuation represent measures that are independent of one another and accordingly can be applied individually or collectively.

Figure 5:
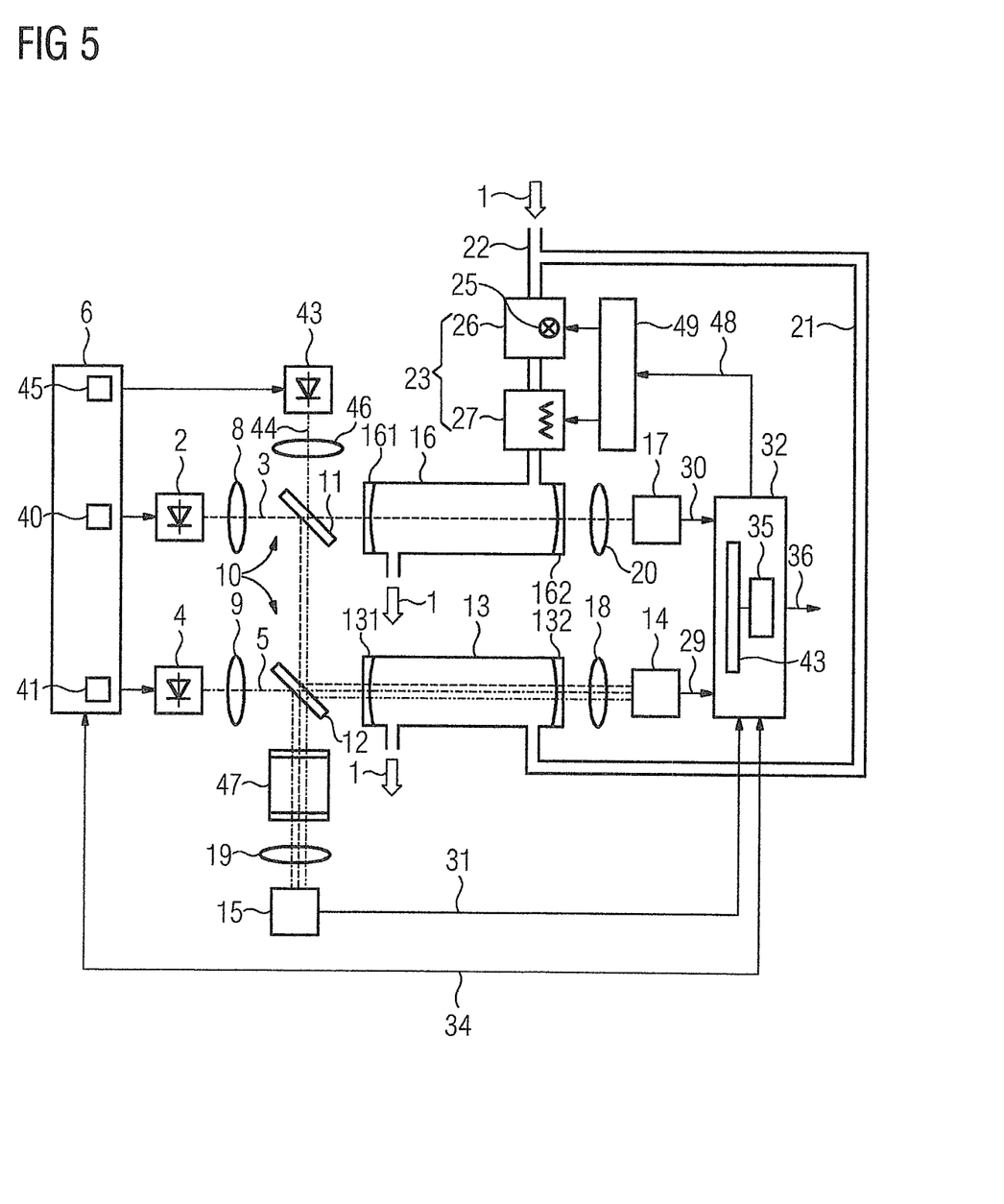
FIG. 5 shows a third exemplary embodiment of the gas analyzer in accordance with the invention for measuring nitrogen oxides, sulfur dioxide and oxygen.

FIG. 5 shows a third exemplary embodiment of the gas analyzer in accordance with the invention, which differs from that of FIG. 1 by, as in the case of the example in FIG. 4, the light 3, 5 of the light-emitting diodes 2, 4 being modulated differently and demodulated accordingly on detection.

Moreover, arranged in the region of the semi-transparent mirror 11, the beam splitter arrangement 10 is a narrowband light source 43 that emits light 44 in the wavelength range of 760 nm to 765 nm. The light source 43 may involve a light-emitting diode or, as in the example shown here, a laser diode, which is actuated by a modulation device 45 with a current ramp, in order to read off an oxygen absorption line, for example at 764 nm, in a wavelength-dependent manner using the generated light 44. In this context, the current can additionally be modulated in a sinusoidal manner. The light 44 is shaped via a collimator lens 46 to form a parallel light bundle, which is split by the mirror 11 into a partial beam through the second measuring chamber 16 to the second detector 17 and a further partial beam to the second semi-transparent mirror 12. Here, the light 44 is split further into a partial beam through the first measuring chamber 13 to the first detector 17 and a further partial beam to the reference detector 15. An optional reference cuvette 47 filled with oxygen additionally enables a reliable wavelength calibration of the laser diode 43. The detection of the light 44 of the light source 43 by way of the detectors 14, 17 leads to further signal components in the detector signals 29, 30, from which the evaluation device 32 ascertains the concentrations of oxygen in the exhaust gas 1 in the two measuring chambers 13, 16 and output these as part of the analysis result 36. In this context, the concentration of oxygen in the untreated exhaust gas is measured in the first measuring chamber 13 and the concentration of oxygen in the treated exhaust gas, i.e., after the generation of the oxygen the and conversion of nitrogen monoxide into nitrogen dioxide taking place accordingly, is measured in the second measuring chamber 16. The difference between both oxygen measurements therefore indicates the amount of oxygen consumed as part of the conversion of nitrogen monoxide into nitrogen dioxide and is therefore a measure of the degree of conversion. This information can also be used as a control signal 48 for a control device 49 of the oxidation device 23. Thus, for example, the performance of the ultraviolet light source 25 or the heating performance for the gas heating in the heating chamber 27 can be optimized or regulated. As a result of the low absorption cross-section when measuring oxygen, the measuring chambers 13, 16 can be embodied as multipass cells, where instead of windows highly reflective concave mirrors 131, 132, 161, 162 are installed, which are transparent for the wavelengths of the light-emitting diodes 2 and 4.

Figure 6:
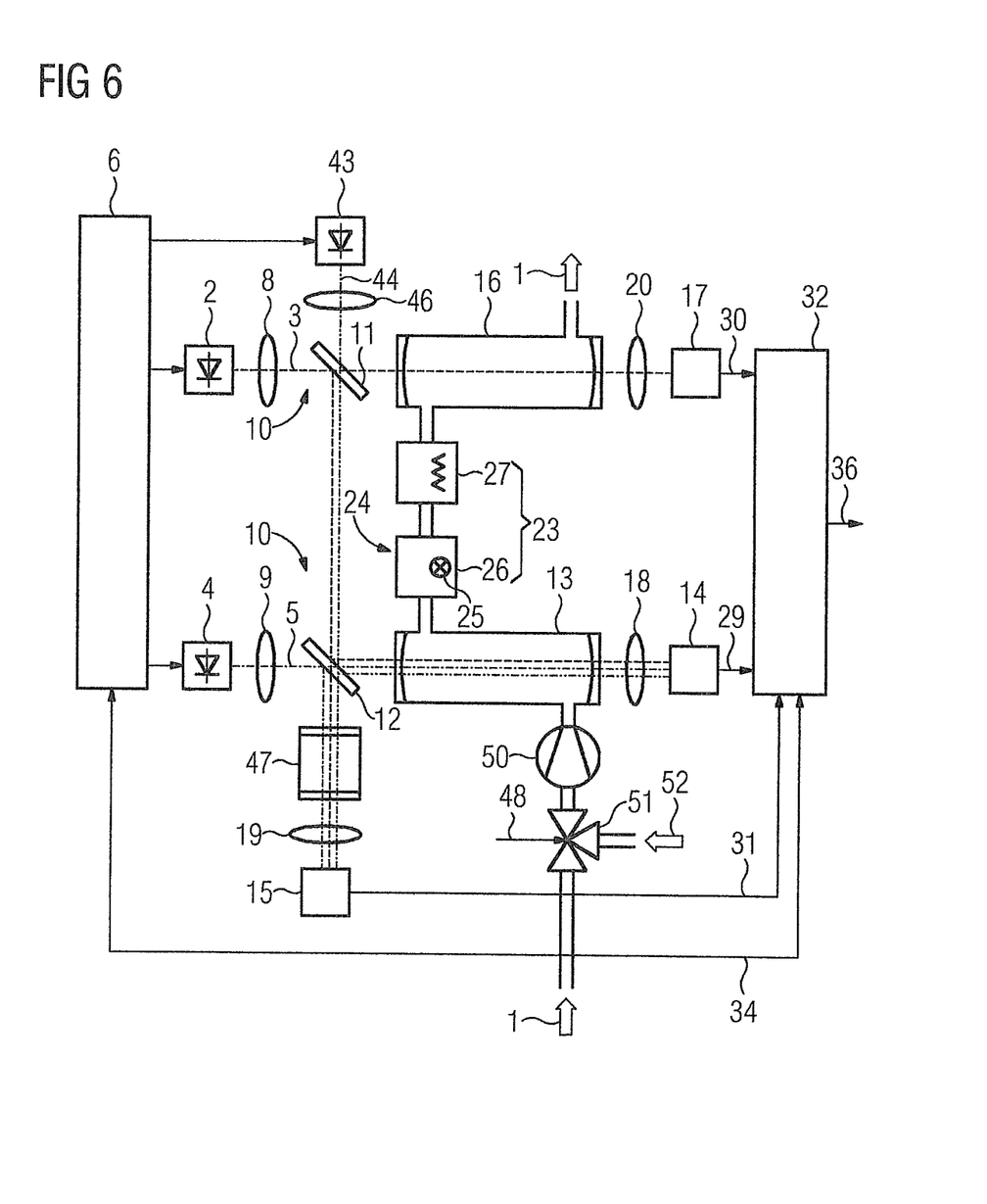
FIG. 6 shows a fourth exemplary embodiment of the gas analyzer in accordance with the invention for measuring nitrogen oxides, sulfur dioxide and oxygen.

FIG. 6 shows a modified version of the exemplary embodiment in FIG. 5, in which the first measuring chamber 13, the oxidation device 23 and the second measuring chamber 16 are connected in series and in succession. The exhaust gas 1 is thus not split into two partial flows through the two measuring chambers 13, 17, but rather is guided through the first measuring chamber 13 first untreated and then treated, in order to finally flow through the second measuring chamber 17. The flowing of the exhaust gas 1 through the gas analyzer is generated and regulated via a gas pump 50. A controllable three-path mixing valve 51 is arranged in the path of the exhaust gas upstream of the first measuring chamber 13, in order to be able to admix the exhaust gas 1 with atmospheric oxygen 52 when the residual oxygen content of the exhaust gas 1 or the performance of the ozone generator 24 is not sufficient for the ozone generation required for complete conversion of nitrogen monoxide into nitrogen dioxide. The admixing may occur manually or automatically as a function of the control signal 48 (see FIG. 5).

Thus, while there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A gas analyzer for measuring nitrogen oxides and sulfur dioxide in an exhaust gas, comprising:
   a first light-emitting diode radiating in a near-ultraviolet range between 350 nm and 500 nm;
   a second light-emitting diode radiating in a middle-ultraviolet range between 250 nm and 300 nm
   a first measuring chamber, through which the exhaust gas flows and which is irradiated by light of the first and second light-emitting diodes;
   a first detector which detects the light of the first and second light-emitting diodes after irradiation of the measuring chamber and which generates a first detector signal with a first signal component resulting from the light of the first light-emitting diode and a second signal component resulting from the light of the second light-emitting diode;
   an evaluation device which utilizes the first signal component to ascertain a concentration of nitrogen dioxide and which utilizes the second signal component to ascertain a concentration of sulfur dioxide in exhaust gas in the first measuring chamber;
   an oxidation device which treats the exhaust gas with ozone to convert nitrogen monoxide contained in the exhaust gas into nitrogen dioxide;
   a second measuring chamber connected to the oxidation device, through which the treated exhaust gas flows, while untreated exhaust gas flows through the first measuring chamber;
   a beam splitter arrangement which splits off part of the light of the first light-emitting diode through the second measuring chamber to a second detector, and which generates a second detector signal with a first signal component resulting from the light of the first light-emitting diode;
   wherein the evaluation device further determines a concentration of nitrogen dioxide in the exhaust gas in the second measuring chamber from the first signal component of the second detector signal and outputs said determined concentration as the concentration of nitrogen oxide in the exhaust gas and outputs a difference in the concentration of nitrogen dioxide ascertained in the first and second measuring chambers as the concentration of nitrogen monoxide.

2. The gas analyzer as claimed in claim 1, further comprising:
   a narrowband light source which radiates in a wavelength range of 760 nm to 765 nm, the light thereof being conducted by the beam splitter arrangement through both measuring chambers to the two detectors and resulting in further signal components of the detector signals;
   wherein the evaluation device utilizes the further signal component of the first detector signal to ascertain the concentration of oxygen in the untreated exhaust gas in the first measuring chamber and utilizes the further signal component of the second detector signal to ascertain the concentration of oxygen in the treated exhaust gas in the second measuring chamber and, based on ascertained the concentration of oxygen in the untreated exhaust gas and ascertained the concentration of oxygen in the treated exhaust gas, monitors the conversion of the nitrogen monoxide into nitrogen dioxide in the oxidation device.

3. The gas analyzer as claimed in claim 2, wherein the narrowband light source comprises one of (i) a wavelength-tunable laser diode and (ii) a light-emitting diode with a downstream filter.

4. The gas analyzer as claimed in claim 2, wherein the measuring chambers are formed as multi-pass cells with highly reflective concave mirrors which are transparent for wavelengths of the first and second light-emitting diodes.

5. The gas analyzer as claimed in claim 3, wherein the measuring chambers are formed as multi-pass cells with highly reflective concave mirrors which are transparent for wavelengths of the first and second light-emitting diodes.

6. The gas analyzer as claimed in claim 1, wherein the beam splitter arrangement is configured to split off part of the light of the first and second light-emitting diodes and, if present, a narrowband light source to a reference detector, which generates a reference signal using reference signal components resulting from the light of the light-emitting diodes and, where required, the narrowband light source; and wherein the evaluation device references signal components of detector signals with associated reference signal components.

7. The gas analyzer as claimed in claim 1, wherein the oxidation device includes an ozone generator in a reaction chamber through which the exhaust gas flows and a heating chamber downstream of said reaction chamber; and wherein the ozone generator is configured to generate ozone from the oxygen content of the exhaust gas.

8. The gas analyzer as claimed in claim 7, wherein the oxidation device comprises an ultraviolet light source.

9. The gas analyzer as claimed in claim 7, further comprising:
   a mixing valve arranged in the exhaust gas path upstream of the first measuring chamber and the oxidation device, said a mixing valve being configured to admix the exhaust gas with atmospheric oxygen.

* * * * *